(12) United States Patent
Jung et al.

(10) Patent No.: US 12,220,573 B2
(45) Date of Patent: Feb. 11, 2025

(54) ELECTRODE-ELECTRICAL CONDUCTOR SYSTEM FOR A MEDICAL DEVICE

(71) Applicant: Heraeus Deutschland GmbH & Co. KG, Hanau (DE)

(72) Inventors: Markus Jung, Hanau (DE); Thorsten Kaiser, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 722 days.

(21) Appl. No.: 17/514,505

(22) Filed: Oct. 29, 2021

(65) Prior Publication Data
US 2022/0134088 A1    May 5, 2022

(30) Foreign Application Priority Data

Oct. 29, 2020  (EP) ................................ 20204547

(51) Int. Cl.
*A61N 1/05*     (2006.01)
*H01R 4/02*     (2006.01)

(52) U.S. Cl.
CPC ............. *A61N 1/056* (2013.01); *H01R 4/026* (2013.01); *H01R 4/029* (2013.01)

(58) Field of Classification Search
CPC .......... A61N 1/056; A61N 1/05; A61N 1/048; H01R 4/026; H01R 4/029
See application file for complete search history.

(56) References Cited

U.S. PATENT DOCUMENTS

| | | | | |
|---|---|---|---|---|
| 5,545,219 | A * | 8/1996 | Kuzma | A61F 11/20 607/137 |
| 7,239,922 | B1 | 7/2007 | Boogaard et al. | |
| 7,904,180 | B2 | 3/2011 | Juola et al. | |
| 8,756,806 | B2 * | 6/2014 | O'Dea | A61M 25/1027 156/60 |
| 9,789,305 | B2 * | 10/2017 | Frericks | A61N 1/0541 |

(Continued)

FOREIGN PATENT DOCUMENTS

| | | |
|---|---|---|
| EP | 3 185 248 | 6/2017 |
| EP | 3 185 363 | 6/2017 |

(Continued)

OTHER PUBLICATIONS

"Parts of an Electrical Cable, Top Cable", Sep. 16, 2020, pp. 1-6, XP093164028, retrieved from the Internet: https://www.topcable.com/blog-electric-cable/en/parts-of-an-electrical-cable/.

*Primary Examiner* — Travis S Chambers
(74) *Attorney, Agent, or Firm* — Dicke, Billig & Czaja, PLLC

(57) ABSTRACT

One aspect relates to an electrode-electrical conductor system for a medical device. The system includes one or more electrically insulated wire(s) or cable(s) wherein. The electrical insulation includes electrical conductor one or more partial opening(s), which is/are arranged on one side of the wire(s) or cable(s), and one or more electrode(s), which is/are mechanically and electrically connected to the wire(s) or cable(s) via the one or more partial opening(s) arranged on one side of the wire(s) or cable(s). The mechanical and electrical connections are made by welding, pressing, swaging, adhesives, brazing, soldering and/or dimples. One aspect also relates to a method for preparing such an electrode-electrical conductor system.

16 Claims, 2 Drawing Sheets

(56) References Cited

U.S. PATENT DOCUMENTS

| | | | |
|---|---|---|---|
| 10,487,377 B2* | 11/2019 | Richter | ........... C22C 30/00 |
| 2002/0038139 A1 | 3/2002 | Wessman et al. | |
| 2020/0009370 A1 | 1/2020 | Julien et al. | |

FOREIGN PATENT DOCUMENTS

| | | |
|---|---|---|
| EP | 3 666 327 | 6/2020 |
| WO | 99/49932 | 10/1999 |
| WO | 2015/031265 | 3/2015 |

\* cited by examiner

ELECTRODE-ELECTRICAL CONDUCTOR SYSTEM FOR A MEDICAL DEVICE

CROSS-REFERENCE TO RELATED APPLICATION

This Utility Patent Application claims priority to European Application No. 20 204 547.2 filed on Oct. 29, 2020, which is incorporated herein by reference.

TECHNICAL FIELD

One aspect relates to an electrode-electrical conductor system for a medical device including a) at least one electrical conductor including one or more electrically insulated wire(s) or cable(s), wherein the electrical insulation includes one or more partial opening(s), which is/are arranged on one side of the wire(s) or cable(s), and b) one or more electrode(s), which is/are mechanically and electrically connected to the wire(s) or cable(s) via the one or more partial opening(s) arranged on one side of the wire(s) or cable(s) by welding, pressing, swaging, adhesives, brazing, soldering and/or dimples. One embodiment also relates to a method for preparing such an electrode-electrical conductor system.

BACKGROUND

Medical devices, and especially active implantable medical devices, contain electrodes to electrically stimulate body tissue such as muscles and nerves.

The electrical contacting of an electrical conductor to an electrode can often be a major challenge, in one embodiment if dimensions are small such as in medical devices which are introduced in the human or animal body. Furthermore, e.g., good electrical conductivity and mechanical stability even upon exposure to strong loads over an extended period of time are desired.

Another very important feature is the reliability of medical devices such as, e.g., cardiac pacemakers, implantable cardioverters, defibrillation devices, and cardiac resynchronisation devices, particularly with a view to keeping the material fatigue as low as possible. In particular the electrical conductor and the connection to the electrode are exposed to strong loads in operation. Since invasive surgery is commonly required in order to introduce medical devices into the body or to remove or replace parts thereof, the individual components of the device are therefore desired to have a long service life in order to reduce the need for surgical interventions.

Methods for connecting an electrical conductor to an electrode are known in the art. For example, US 2020/0009370 A1 refers to a method for connecting a strand of a multi-strand cable to an electrode of an implantable medical device. The method includes cutting a strand of a multi-strand cable, lifting at least one of the free ends, stripping the end of the lifted strand, placing an electrode around the multi-strand cable to partially cover the end of the lifted and stripped stand, and connecting at least one portion of the stripped end of the strand to the electrode.

Conventional methods have the drawback that the whole electrical conductor including the insulation is cut in order to connect the electrical conductor to the electrode. However, it is typically not possible to properly connect the electrical conductor to the electrode in a flush-fitted manner such that parts of the cut electrical conductor are in contact with surrounding materials. This may result in decreased electrical conductivity and service life.

In view of the above, there is still a need for an electrode-electrical conductor system for a medical device. Furthermore, it is desired that the electrical conductor includes selective openings such that the electrode can be assembled via these openings in a flush-fitted manner. It is additionally desired that the electrode-electrical conductor system can be easily manufactured, i.e. without complex manufacturing steps and equipment.

Therefore, one aspect is directed to the provision of an improved, or at least alternative, electrode-electrical conductor system for a medical device and a method for preparing such an electrode-electrical conductor system for a medical device.

SUMMARY

The foregoing and other objects are solved by the subject-matter as defined in the independent claims. Advantageous embodiments are defined in the corresponding subclaims.

One embodiment provides an electrode-electrical conductor system for a medical device including a) at least one electrical conductor including one or more electrically insulated wire(s) or cable(s), wherein the electrical insulation includes one or more partial opening(s), which is/are arranged on one side of the wire(s) or cable(s), and b) one or more electrode(s), which is/are mechanically and electrically connected to the wire(s) or cable(s) via the one or more partial opening(s) arranged on one side of the wire(s) or cable(s) by welding, pressing, swaging, adhesives, brazing, soldering and/or dimples.

The inventors surprisingly found out that the electrode-electrical conductor system is suitable for a medical device. Furthermore, the electrode can be assembled to the electrical conductor via selective partial openings in a flush-fitted manner. Moreover, it has been found out that the partial opening of the electrical insulation is of great advantage as it increases the dielectric strength/resistance against electrical short circuits towards other insulated conductors within the electrode-electrical conductor system. Moreover, the electrode-electrical conductor system can be easily manufactured without complex manufacturing steps and equipment.

According to one embodiment, the electrical conductor includes one or more bundle(s) or strand(s) of electrically insulated wire(s) or cable(s), in one embodiment each of the one or more bundle(s) or strand(s) of electrically insulated wire(s) or cable(s) is/are covered by an electrical insulation, which, if present, includes one or more opening(s) arranged on the one or more partial opening(s) on one side of the wire(s) or cable(s).

According to one embodiment, the wire(s) or cable(s) of the electrical conductor and/or the at least one electrode include(s) one or more of the metals Pt, Ir, Ta, Pd, Ti, Fe, Au, Mo, Nb, W, Ni, Ti, Ag, Cu, or a mixture and/or alloy thereof and/or the electrical conductor and/or the at least one electrode is/are a multilayered material system(s).

According to one embodiment, the electrical insulation of the electrical conductor includes an insulating plastic material, in one embodiment an insulating plastic material selected from the group including polyethylene, polyurethane, polyimide, polyamide, PEEK, and fluorinated plastic materials such as ETFE, PTFE, PFA, PVDF, FEP or FPO, and mixtures thereof.

According to one embodiment, the wire(s) or cable(s) has/have a thickness in the range from 5 to 250 µm, in one embodiment from 10 to 120 μm, and/or the electrical insulation of the wire(s) or cable(s) has/have a thickness in the range from 3 to 150 μm, in one embodiment from 5 to 70 μm.

According to one embodiment the wire(s) or cable(s) within the one or more partial opening(s) is/are mechanically or laser cut such that one or both of the free ends of the cut wire(s) or cable(s) is/are connected to the one or more electrode(s).

According to one embodiment, one or both of the free ends of the cut wire(s) or cable(s) is/are pressed or welded.

According to one embodiment, the one or more electrode(s) is/are selected from a cubic, rectangular, cylindrical and ring electrode and ring electrode segment, in one embodiment a ring electrode or ring electrode segment.

According to one embodiment, the electrical conductor is embedded in a polymer substrate, in one embodiment a biocompatible polymer substrate, in one embodiment a biocompatible polymer substrate is selected from the group including polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), kapton and mixtures thereof, including one or more opening(s) arranged on the one or more partial opening(s) on one side of the wire(s) or cable(s).

According to a further embodiment, a method for preparing an electrode-electrical conductor system for a medical device as defined herein is provided, the method including the steps of
  a) providing at least one electrical conductor including one or more wire(s) or cable(s) which is/are surrounded by an electrical insulation,
  b) partially opening the electrical insulation of the at least one electrical conductor by laser ablation or mechanical cutting such as to obtain one or more opening(s) on one side of the wire(s) or cable(s), wherein the wire(s) or cable(s) are cut or uncut, and
  c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

According to one embodiment, the method includes a further step of cutting the one or more wire(s) or cable(s) by laser cutting or mechanical cutting to obtain two free ends at the cut of the wire(s) or cable(s) before attaching the one or more electrode(s) to the one or more partial opening(s) of the at least one electrical conductor.

According to one embodiment, the method includes a further step of lifting one or both of the free ends relative to the rest of the one or more wire(s) or cable(s) before attaching the one or more electrode(s) to the one or more partial opening(s) of the at least one electrical conductor.

According to one embodiment, the partial opening of the electrical insulation by laser ablation or mechanical cutting is carried out such that the wire(s) or cable(s) are uncut, and/or the further step of cutting the one or more wire(s) or cable(s) by laser cutting or mechanical cutting is carried out such that the remaining electrical insulation surrounding the wire(s) or cable(s) is uncut.

According to one embodiment, the method includes a further step of pressing or welding one or both of the free ends, in one embodiment both of the free ends.

According to one embodiment, step b) further includes opening a polymer substrate in which the electrical conductor is embedded by laser ablation or mechanical cutting.

It should be understood that for the purposes of the present embodiments, the following terms have the following meanings:

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present embodiments, the terms "essentially consisting of" and "consisting of" are considered to be a preferred embodiment of the term "comprising". If hereinafter a group is defined to comprise at least a certain number of embodiments, this is also to be understood to disclose a group, which in one embodiment essentially consists of only of these embodiments, or in one embodiment consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The following schematic drawings illustrate aspects of the embodiments for improving the understanding of the invention in connection with some exemplary illustrations, wherein.

DETAILED DESCRIPTION

In the following Detailed Description, reference is made to the accompanying drawings, which form a part hereof, and in which is illustrated by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

Figure 1:
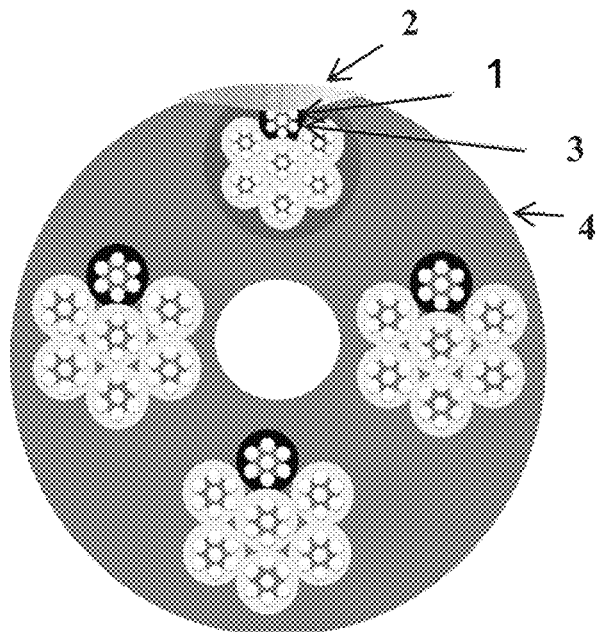
FIG. 1 illustrates one embodiment of the electrode-electrical conductor system according to one embodiment in a cross-sectional view.

FIG. 1 illustrates one embodiment of the electrode-electrical conductor system according to one embodiment in a cross-sectional view. The electrical conductor of FIG. 1 includes four bundles of electrical conductors and each bundle includes seven electrically insulated wire(s) or cable(s) (1). In this embodiments, each bundle is surrounded by an electrical insulation (3). Furthermore, the group of bundles is again surrounded by or embedded into an electrical insulation (4). The electrical insulation of one of the electrical conductor includes a partial opening obtained via laser ablation (2). Furthermore, the electrical insulation (3) surrounding the bundle includes an opening obtained via laser ablation (2). In addition thereto, the electrical insulation (4) surrounding the group of bundles includes an opening obtained via laser ablation (2). The openings in the electrical insulation (3) surrounding the bundle and in the electrical insulation (4) surrounding the group of bundles are such that the wire in the electrical conductor can be easily reached such as to cut the wire and to lift up one or both of the free ends relative to the rest of the wires in order to connect one or more electrode(s) to the wire for obtaining the electrode-electrical conductor system. In one embodiment, the one or more electrode(s) can be connected to the uncut wire.

Figure 2A:
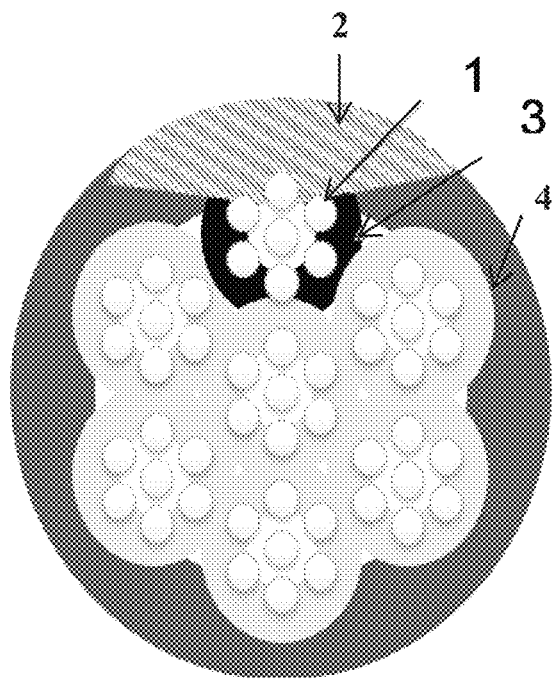
FIG. 2 illustrates a further embodiment of the electrode-electrical conductor system according to an embodiment in a cross-sectional view.
Figure 2B:
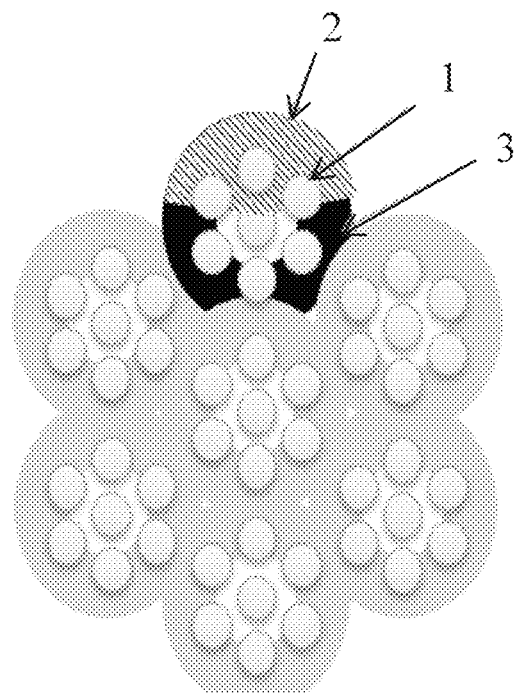

FIGS. 2a-2b illustrate a further embodiment of the electrode-electrical conductor system according to an embodiment in a cross-sectional view. The electrical conductor of FIG. 2 includes seven bundles of electrical conductors and each bundle includes seven electrically insulated wire(s) or cable(s) (1). In FIG. 2a, each bundles is surrounded by an electrical insulation (3). Furthermore, the group of bundles is again surrounded by or embedded into an electrical insulation (4). The electrical insulation of one of the electrical conductors includes partial opening obtained via laser ablation (2). Furthermore, the electrical insulation (3) surrounding the bundle includes an opening obtained via laser ablation (2). In addition thereto, the electrical insulation (4) surrounding the group of bundles includes an opening obtained via laser ablation (2). The openings in the electrical insulation (3) surrounding the bundle and in the electrical insulation (4) surrounding the group of bundles are such that the wire in the electrical conductor can be easily reached such as to cut the wire and to lift up one or both of the free ends relative to the rest if the wires in order to connect one or more electrode(s) to the wire for obtaining the electrode-electrical conductor system. In one embodiment, the one or more electrode(s) can be connected to the uncut wire. In FIG. 2b, each bundle is surrounded by an electrical insulation (3). The electrical insulation of one of the electrical conductors includes a partial opening obtained via laser ablation (2). Furthermore, the electrical insulation (3) surrounding the bundle includes an opening obtained via laser ablation (2). The opening in the electrical insulation (3) surrounding the bundle is such that the wire in the electrical conductor can be easily reached such as to cute the wire and t lift up one or both of the free ends relative to the rest of the wires in order to connect one or more electrode(s) to the wire for obtaining the electrodes-electrical conductor system. In one embodiment, the one or more electrode(s) can be connected to the uncut wire.

Figure 3:
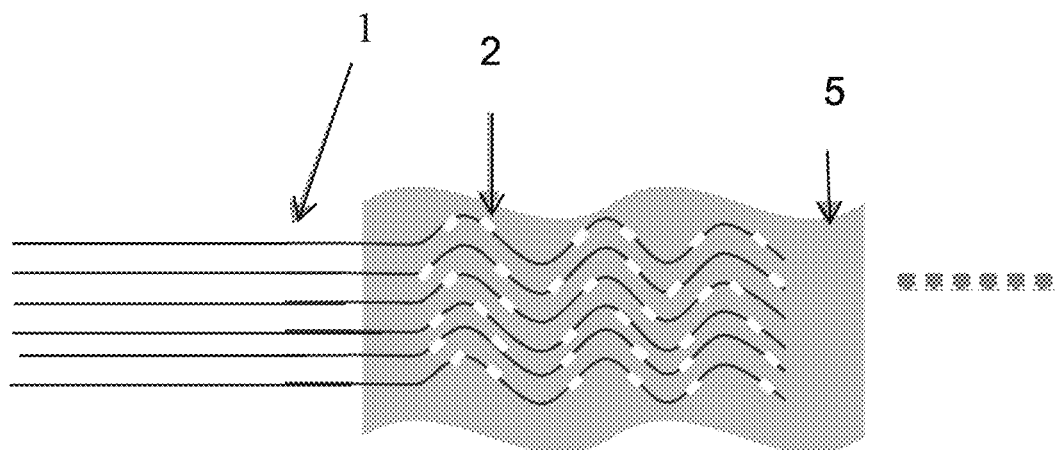
FIG. 3 illustrates a further embodiment of the electrode-electrical conductor system according to an embodiment in a top an cross-sectional view.

FIG. 3 illustrates a further embodiment of the electrode-electrical conductor system according to an embodiment in a top and cross-sectional view. The electrical conductor of FIG. 3 is made up of several electrical conductor including single wires which are electrically isolated (1). Furthermore, the electrical conductor are embedded into a biocompatible polymer substrate (5). The electrical insulation of the electrical, conductors include a partial opening obtained via laser ablation (2). Furthermore, the biocompatible polymer substrate (5) in which the electrical conductor is embedded includes a partial opening obtained via laser ablation (2). The openings in the biocompatible polymer substrate (5) are such that the wire in the electrical conductor can be easily reached such as to cut the wire and to lift up one or both of the free ends relative to the rest of the wires in order to connect one or more electrode(s) to the wire for obtaining the electrode-electrical conductor system. In one embodiment, the one or more electrode(s) can be connected to the uncut wire.

One aspect of the one embodiment refers to an electrode-electrical conductor system for a medical device including a) at least one electrical conductor including one or more electrically insulated wire(s) or cable(s), wherein the electrical insulation includes one or more partial opening(s), which is/are arranged on one side of the wire(s) or cable(s), and b) one or more electrode(s), which is/are mechanically and electrically connected to the wire(s) or cable(s) via the one or more partial opening(s) arranged on one side of the wire(s) or cable(s) by welding, pressing, swaging, adhesives, brazing, soldering and/or dimples.

It is thus required that the electrode-electrical conductor system includes at least one electrical conductor.

The term "at least one" electrical conductor in the meaning of one embodiment means that the electrical conductor includes, in one embodiment consists of, one or more electrical conductor(s).

In one embodiment, the electrical conductor includes, in one embodiment consists of, one electrical conductor. In one embodiment, the electrical conductor includes, in one embodiment consists of, two or more electrical conductors. For example, the electrical conductor includes, in one embodiment consists of, one electrical conductor.

It is further appreciated that the at least one electrical conductor includes one or more electrically insulated wire(s) or cable(s). That is to say, each electrical conductor includes one or more electrically insulated wire(s) or cable(s).

It is to be noted that a cable is a regular structure of multiple wires, which are twisted.

In one embodiment, the electrically insulated wire or cable has a thickness ranging from 20 to 400 μm, in one embodiment ranging from 40 to 190 μm.

It is to be noted that the wire(s) or cable(s), i.e. without electrical insulation, in one embodiment has/have a thickness in the range from 5 to 250 μm, in one embodiment from 15 to 190 μm.

Additionally or in one embodiment, the electrical insulation of the wire(s) or cable(s) has/have a thickness in the range from 3 to 150 μm, in one embodiment from 5 to 70 μm.

In one embodiment, the wire(s) or cable(s), i.e. without electrical insulation, has/have a thickness in the range from 5 to 250 μm, in one embodiment from 15 to 190 μm or the electrical insulation of the wire(s) or cable(s) has/have a thickness in the range from 3 to 150 μm, in one embodiment from 5 to 70 µm. In one embodiment, the wire(s) or cable(s), i.e. without electrical insulation, has/have a thickness in the range from 5 to 250 µm, in one embodiment from 15 to 190 µm and the electrical insulation of the wire(s) or cable(s) has/have a thickness in the range from 3 to 150 µm, in one embodiment from 5 to 70 µm.

It is to be noted that the one or more electrically insulated wire(s) or cable(s) can be round cable(s) or wire(s), i.e. the thickness of the cable(s) or wire(s) in all dimensions is almost the same. In one embodiment, the one or more electrically insulated wire(s) or cable(s) can be flat cable(s) or wire(s), i.e. the thickness of the cable(s) or wire(s) in one dimension is reduced compared to the other dimensions.

In one embodiment, the one or more electrically insulated wire(s) or cable(s) is a/are round cable(s) or wire(s).

The at least one electrical conductor includes one or more electrically insulated wire(s) or cable(s). Accordingly, the at least one electrical conductor includes one or more metal wire(s) or cable(s) and an insulation or consists of one or more metal wire(s) or cable(s) and an insulation. In some embodiments, the at least one electrical conductor includes one or more of the metals Pt, Ir, Ta, Pd, Ti, Fe, Au, Mo, Nb, W, Ni, Ti, Ag, Cu, or a mixture and/or alloy thereof. In some embodiments, the at least one electrical conductor includes Pt alloys such as PtIr10 and PtIr20, or the alloys MP35N, MP35N—Ag, 316L, 301, SST (stainless steel) or nitinol.

In one embodiment, the at least one electrical conductor includes MP35, Cu, Au, Ta, Pt, Ir or Pd. In some embodiments, the electrically conductive part of the at least one electrical conductor consists of MP35N, MP35N—Ag, SST (stainless steel), Cu, Au, Ta, Pt, Ir or Pd or alloys of the metals. In some embodiments, the at least one electrical conductor contains less than 3%, 2% or less than 1% Fe.

MP35N is a nickel-cobalt-based hardenable alloy. A variant of MP35N is described in the industrial standard ASTM F562-13. In one embodiment, MP35N is an alloy that includes 33 to 37% Co, 19 to 21% Cr, 9 to 11% Mo, and 33 to 37% Ni.

PtIr10 is an alloy made of 88 to 92% platinum and 8 to 12% iridium.

PtIr20 is an alloy made of 78 to 82% platinum and 18 to 22% iridium.

316L is an acid-resistant, CrNiMo austenitic steel with approx. 17% Cr; approx. 12% Ni and at least 2.0% Mo. One variant of 316L is described in the industrial standard EN 10088-2. In one embodiment, 316L is an alloy that includes 16.5 to 18.5% Cr, 2 to 2.5% Mo, and 10 to 13% Ni.

301 is a chromium-nickel steel with high corrosion resistance. One variant of 301 is described in the industrial standard DIN 1.4310. In one embodiment, 301 is an alloy that includes 16 to 18% Cr and 6 to 8% Ni.

Nitinol is a nickel-titanium alloy with a shape memory with an ordered-cubic crystal structure and a nickel fraction of approximately 55%, whereby titanium accounts for the remaining fraction. Nitinol has good properties with regard to biocompatibility and corrosion resistance.

Unless specified otherwise, all percentages given herein shall be understood to be mass percentages (weight %).

It is appreciated that the at least one electrical conductor should have a high electrical conductivity and low electrical resistance. Thus, the at least one electrical conductor in one embodiment includes one or more wire(s) or cable(s) made from Pt or Pt alloy, MP35N, MP35N—Ag, or SST (stainless steel).

The at least one electrical conductor may also include multilayered material systems.

It is preferred that the electrically conductive part of the at least one electrical conductor, i.e. the wire or cable, consists of one or more of the materials and an insulation.

The at least one electrical conductor is electrically insulated, in one embodiment by an insulating plastic material. In as far as multiple electrical conductors or more than one electrically insulated wire(s) or cable(s) are present, these include no electrical connection to each other. In some embodiments, the at least one electrical conductor includes a dielectric sheathing, for example made of an electrically insulating plastic material, silicone or rubber. Suitable insulating plastic materials are selected from the group including polyethylene, polyurethane, polyimide, polyamide, PEEK, and fluorinated plastic materials such as ETFE, PTFE, PFA, PVDF, FEP or FPO, and mixtures thereof. In one embodiment, the insulating plastic material is selected from the group including polyurethane and fluorinated plastic materials such as ETFE, PTFE or PFA.

A plurality of electrically insulated wire(s) or cable(s) can be arranged into a conductor bundle or strand. It is also appreciated that the electrical conductor may include several bundle(s) or strand(s) of electrically insulated wire(s) or cable(s).

In one embodiment, the electrical conductor thus includes one or more bundle(s) or strand(s) of electrically insulated wire(s) or cable(s).

It is appreciated that the term "bundle" refers to multiple wires or cables which are randomly bundled. The term "strand" refers to multiple wires or cables which are regular twisted structures.

For the sake of completeness, it is to be noted that each wire or cable in such a bundle or strand is electrically insulated. Thus, the at least one electrical conductor may be in the form of a bundle or strand of electrically insulated wire(s) or cable(s), wherein each wire or cable is electrically insulated.

It is also possible that each of the one or more bundle(s) or strand(s) of electrically insulated wire(s) or cable(s) is surrounded by an outer electrical insulation covering each of the one or more bundle(s) or strand(s) of electrically insulated wire(s) or cable(s). Such an outer insulation in one embodiment has a thickness in the range from 5 to 150 µm, in one embodiment from 10 to 80 µm.

It is to be noted that the thickness of such an outer insulation of the bundle(s) or strand(s) can be adjusted to the electrode used in order to avoid e.g. assembling of bridging or spacer elements.

It is further to be noted that the electrical insulation of the at least one electrical conductor includes one or more partial opening(s) which is/are arranged on one side of the wire(s) or cable(s). That is to say, the one or more partial opening(s) are such that they are only partially surrounding the wire(s) or cable(s), i.e. the electrical insulation surrounding the at least one electrical conductor is not completely removed.

The one or more partial opening(s) is/are suitable for mechanically and electrically connecting the at least one electrode of the electrical conductor of the electrode-electrical conductor system.

The number of partial opening(s) in the electrical insulation of the at least one electrical conductor depends on the number of electrodes connected to the at least one electrical conductor.

Thus, the at least one electrical conductor may include one partial opening in the electrical insulation of the at least one electrical conductor. In this case, only one electrode is connected to the at least one electrical conductor.

In one embodiment, the at least one electrical conductor includes two or more partial openings, e.g. two to ten partial openings, in the electrical insulation of the at least one electrical conductor. In this case, two or more, e.g. two to ten, electrodes are connected to the at least one electrical conductor.

Thus, it is preferred that the number of partial openings in the electrical insulation of the at least one electrical conductor corresponds to the number of electrodes connected to the at least one electrical conductor.

If the electrode-electrical conductor system includes more than one electrical conductor, it is appreciated that each electrical conductor may include a different number of partial opening(s), i.e. also a different number of electrodes. However, it is preferred that each electrical conductor in such an arrangement includes the same number of partial opening(s).

It is preferred that the electrode surrounds the entire circumference of the partial opening of the at least one electrical conductor to which the electrode is connected to. This is advantageous in that the wire(s) or cable(s) within the electrical conductor are not exposed to surrounding materials such as tissue resulting in increased electrical conductivity and service life. Thus, the length and diameter of the partial opening(s) is in one embodiment adjusted to the length and diameter of the electrode connected to the electrical conductor.

In one embodiment, the partial opening(s) includes a varying diameter. For example, the opening(s) can be cone-shaped.

In one embodiment, the diameter of the partial opening(s) is/are in the range from 5 to 250 μm, in one embodiment from 10 to 120 μm.

For example, the diameter of the partial opening(s) correspond(s) to the diameter of the wire(s) or cable(s) within the electrical conductor. In one embodiment, the diameter of the partial opening(s) correspond(s) to the diameter of electrically insulated wire(s) or cable(s). In one embodiment, the diameter of the partial opening(s) correspond(s) to the diameter of the wire(s) or cable(s) within the electrical conductor.

It is appreciated the size and shape of the one or more partial opening(s) is selected in a way that the part of the electrical insulation of the at least one electrical conductor, which is in contact with the electrical insulation of an electrical conductor of another conducting channel, remains intact. Thus, the remaining electrical insulation layer of the at least one electrical conductor, which e.g. points radially inwards to the (center of the wire or cable) or points towards the electrical conductor(s) of another conducting channel is intact and functional. Thereby, the dielectric strength/resistance against electrical short circuits is increased. This is one important finding by the inventors.

According to one embodiment, the size of the one or more partial opening(s) in the electrical insulation layer of the at least one electrical conductor, as seen in a cross section, does not exceed 60%, in one embodiment 50%, more in one embodiment 40%, of the perimeter of the at least one electrical conductor.

As already mentioned above, the electrical conductor may include one or more bundle(s) or strand(s) of electrically insulated wire(s) or cable(s). In this embodiment, each of the one or more bundle(s) or strand(s) of electrically insulated wire(s) or cable(s) is in one embodiment surrounded by an outer electrical insulation covering each of the one or more bundle(s) or strand(s) of electrically insulated wire(s) or cable(s).

If such outer insulation is present, it is appreciated that the outer insulation of the one or more bundle(s) or strand(s) include(s) one or more opening(s) arranged on the one or more partial opening(s) on one side of the wire(s) or cable(s). That is to say, the opening(s) in the outer insulation of the one or more bundle(s) or strand(s) encompass(es) the partial opening(s) of the electrical conductor. The opening(s) in the outer insulation of the one or more bundle(s) or strand(s) can be flush-fitted to the partial opening(s) of the electrical conductor or the opening(s) in the outer insulation of the one or more bundle(s) or strand(s) can be broader in diameter than the partial opening(s) of the electrical conductor. The later one has the advantage that the wire(s) or cable(s) within the electrical conductor can be better reached such that this embodiment is preferred. If such outer insulation is present, it is preferred that the outer insulation is ablated or cut circumferentially. This is advantageous as a pocket in the outer insulation is created, which receives the ring-electrode/electrode-segment, such that an isodiametric transition is ensured.

Another required component of the electrode-electrical conductor system is at least one electrode.

The term "at least one" electrode in the meaning of one embodiment means that the electrode includes, in one embodiment consists of, one or more electrode(s).

In one embodiment, the electrode includes, in one embodiment consists of, one electrode. In one embodiment, the electrode includes, in one embodiment consists of, two or more electrode. For example, the electrode includes, in one embodiment consists of, one electrode.

The type of electrode is not particularly limited as long as the electrode is suitable for use in a medical device. For example, the one or more electrode(s) is/are selected from a cubic, rectangular, cylindrical and ring electrode and ring electrode segment. In one embodiment, the one or more electrode(s) is/are a ring electrode or a ring electrode segment.

The electrode is a conductive and electrically conductive element, which can be attached appropriately to the at least one electrical conductor or conductor bundle.

In some embodiments, the at least one electrode includes one or more of the metals Pt, Ir, Ta, Pd, Ti, Fe, Au, Mo, Nb, W, Ni, Ti, Ag, Cu, or a mixture and/or alloy thereof. It is to be noted that the at least one electrode may be in contact with tissue and thus, it is especially preferred that it is made of a biocompatible material. In view of this, it is preferred that the at least one electrode includes the alloys MP35N, PtIr20, PtIr10, PdIr10, 316L, or 301. The electrode can just as well include multilayered material systems. In one embodiment, the electrode consists of one or more of the materials.

In view of the different needs in terms of high electrical conductivity and teak resistance of the at least one electrical conductor on one side and the high biocompatibility of the at least one electrode on the other side, it is preferred that the at least one electrical conductor, i.e. the conductive part of the electrical conductor, and the at least one electrode include different materials.

Thus, it is preferred that the electrically conductive part of the at least one electrical conductor in one embodiment consists of Cu, Pt alloys such as PtIr20 and PtIr10, or the alloys MP35N, MP35N—Ag, SST (304, 306), whereas the at least one electrode includes the alloys MP35N, PtIr20, PtIr10, PdIr10, 316L, or 301.

In one embodiment, the at least one electrode has an external diameter of less than 2 mm, in one embodiment in the range from 100 μm to 2 mm and more in one embodiment from 200 μm to 1.5 mm.

Additionally or in one embodiment, the at least one electrode has a length ranging from 50 μm to 5 mm and more in one embodiment from 100 μm to 2 mm.

It is further to be noted that the electrical insulation of the at least one electrical conductor includes one or more partial opening(s) suitable for mechanically and electrically connecting the at least one electrode of the electrode segment to the at least one electrical conductor of the electrical conductor segment. The mechanical and electrical connection between the at least one electrode and the at least one electrical conductor of the electrical conductor segment can be achieved by welding, pressing, swaging, adhesives, brazing, soldering and/or dimples.

For example, the at least one electrode is/are mechanically and electrically connected to the at least one electrical conductor by welding, pressing, swaging, adhesives, brazing, soldering and/or dimples which are pressed through the partial opening(s) of the electrical insulation of the at least one electrical conductor. In case more than one electrode is connected to the at least one electrical conductor, the connection is in one embodiment the same for all connections present.

The mechanical and electrical connection between the at least one electrode and the at least one electrical conductor is in one embodiment achieved by welding, pressing, brazing and/or soldering such as soft soldering. Additionally or in one embodiment, the mechanical and electrical connection between the at least one electrode and the at least one electrical conductor can be achieved by adhesives and/or dimples which are pressed through the partial opening(s) of the electrical insulation of the at least one electrical conductor.

In one embodiment, the mechanical and electrical connection between the at least one electrode and the at least one electrical conductor is achieved by only one means, i.e. by welding, pressing, swaging, adhesives, brazing, soldering and/or dimples which are pressed through the partial opening(s) of the electrical insulation of the at least one electrical conductor.

In one embodiment, the mechanical and electrical connection between the at least one electrode and the at least one electrical conductor in a firmly-bonded manner. In this case, the mechanical and electrical connection between the at least one electrode and the at least one electrical conductor is in one embodiment a welded connection. The welded connection can be attained, for example, by laser welding. The melting of the conductor in the course of welding can be used to completely close the partial opening within the ring electrode. By this means, the ingress of liquids or other contaminations into the partial opening can be prevented. Moreover, sharp edges or burrs on the external side of the partial opening can be covered and therefore smoothed.

Having an exclusively firmly-bonded connection results in a very stable, durable and very conductive connection between the electrical conductor and the electrode.

In one embodiment, the mechanical and electrical connection between the at least one electrode and the at least one electrical conductor is achieved in a force-locking manner. The force-locking connection can be achieved by e.g. dimples or other mechanical pressing methods known in this field. Several suitable methods are described in EP3185248A1. Comparable methods known in this context to a person skilled in the art can be used as well.

In one embodiment, the mechanical and electrical connection between the at least one electrode and the at least one electrical conductor is achieved in a direct firmly-bonded manner. In one embodiment, the mechanical and electrical connection between the at least one electrode and the at least one electrical conductor is achieved in a direct force-locking manner. In one embodiment, the mechanical and electrical connection between the at least one electrode and the at least one electrical conductor is achieved in a direct firmly-bonded as well as a direct force-locking manner. In one embodiment, the mechanical and electrical connection between the at least one electrode and the at least one electrical conductor is achieved in a direct firmly-bonded manner, but not in a force-locking manner.

It is to be noted that the at least one electrical conductor is in one embodiment connected to the at least one electrode within the opening in a form-fitting manner.

In one embodiment, the at least one electrical conductor is connected to the at least one electrode in a firmly-bonded manner, but not in a force-locking manner. The at least one electrical conductor can just as well be connected to the at least one electrode exclusively in a firmly-bonded manner In one embodiment, the at least one electrode is micro-structured, i.e. it includes surface structures, or a coating. The surface structures can impart a higher and precisely defined roughness to the electrode surface. The surface structures can be generated even before connecting the at least one electrode to the at least one electrical conductor as they are not affected by a force-locking connection. It is also possible to micro-structure the at least one electrode after attaching it to the at least one electrical conductor.

Similarly, it is feasible to use coated electrodes. The coatings are in one embodiment used if the mechanical and electrical connection between the at least one electrode of the electrode segment and the at least one electrical conductor of the electrical conductor segment is of an exclusively firmly-bonded manner. Such a coating is not affected by the inventive contacting of the at least one electrical conductor to the at least one electrode.

The at least one electrode can be structured, for example, by using a laser. In one embodiment, the surface of the at least one electrode is enlarged by roughening the surface. This can take place with a variety of methods, for example by using a laser.

A coating can be affected, for example, by using PVD, CVD or electrochemical deposition, which methods are well known to the skilled person. TiN, Ir, $IrO_x$, Pt or conductive polymers, for example conductive polymers based on thiophene, such as, for example, poly-3,4-ethylenedioxythiophene (PEDOT) or the conductive polymers described in WO/2015/031265, can be used for the coating.

In one embodiment, the electrode-electrical conductor system includes a multitude of electrodes, wherein each is electrically and mechanically connected to exactly one of the electrical conductors, such that the multitude of electrodes can be electrically addressed independent of each other. This means that each of the multitude of electrodes is set up to receive an electrical signal exclusively from exactly one electrical conductor or to emit an electrical signal to the electrical conductor, but not to any of the other electrical conductors. Accordingly, each electrode can be electrically triggered independent of the other electrodes. In one embodiment, other than the direct connection between the at least one conductor and the at least one electrode, there is no further component present that connects the at least one electrical conductor to the at least one electrode in order to establish an electrical and mechanical connection between them. According to one embodiment, a welded or soldered connection or a material forming a connection of this type shall not be understood to be a "component" in this context. A component of this type could, e.g., be an adhesive or dimples, which is attached to the wire or cable of the at least one electrical conductor in order to subsequently connect it to the at least one electrode.

In one embodiment, it is preferred that the at least one electrical conductor is embedded in a polymer substrate.

For example, the at least one electrical conductor is partially embedded in the polymer substrate. In one embodiment, the at least one electrical conductor is essentially completely embedded in the polymer substrate. That is to say, the at least one electrical conductor is in one embodiment essentially completely surrounded by the polymer substrate.

In one embodiment, the at least one electrical conductor together with the one or more electrode(s) connected thereto is embedded in a polymer substrate.

For example, the at least one electrical conductor together with the one or more electrode(s) connected thereto is partially embedded in the polymer substrate. In one embodiment, the at least one electrical conductor together with the one or more electrode(s) connected thereto is essentially completely embedded in the polymer substrate. That is to say, the at least one electrical conductor together with the one or more electrode(s) connected thereto is in one embodiment essentially completely surrounded by the polymer substrate.

If the at least one electrical conductor together with the one or more electrode(s) connected thereto is partially embedded in the polymer substrate, it is preferred that the at least one electrical conductor is partially or essentially completely surrounded by the polymer substrate, whereas the one or more electrode(s) connected thereto is not embedded in the polymer substrate.

The polymer substrate may be any polymeric material known to be suitable for the products to be prepared. For example, the polymer substrate is a biocompatible polymer substrate.

The term "biocompatible" in the meaning of one embodiment is meant to refer to a material which is considered by a person skilled in the art to be safe when being in contact with a living organism (e.g. a human or animal) over a specific period of time (e.g. when used in an implantable medical device).

For example, the biocompatible polymer substrate is selected from the group including polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), kapton and mixtures thereof.

In one embodiment, the biocompatible polymer substrate is polyurethane or silicone. More in one embodiment, the biocompatible polymer substrate is silicone.

It is appreciated that, if such polymer substrate in which the at least one electrical conductor is embedded is present, the polymer substrate includes one or more opening(s) arranged on the one or more opening(s) on one side of the wire(s) or cable(s).

That is to say, the opening(s) in the polymer substrate encompass(es) the partial opening(s) of the electrical conductor. The opening(s) in the polymer substrate can be flush-fitted to the opening(s) of the electrical conductor or the opening(s) in the polymer substrate can be broader in diameter than the partial opening(s) of the electrical conductor. The later one has the advantage that the wire(s) or cable(s) within the electrical conductor can be better reached such that this embodiment is preferred.

If the at least one electrical conductor is in the form of bundle(s) or strand(s) of electrically insulated wire(s) or cable(s) and includes an outer insulation, the opening(s) in the polymer substrate encompass(es) the partial opening(s) in the outer insulation of the one or more bundle(s) or strand(s) and the partial opening(s) of the at least one electrical conductor.

In this embodiment, the opening(s) in the polymer substrate can be flush-fitted to the partial opening(s) in the outer insulation of the one or more bundle(s) or strand(s) or the partial opening(s) in the polymer substrate can be broader in diameter than the partial opening(s) in the outer insulation of the one or more bundle(s) or strand(s). The later one has the advantage that the wire(s) or cable(s) within the electrical conductor can be better reached such that this embodiment is preferred.

In view of the above, it is appreciated that the wire(s) or cable(s) of electrically insulated wire(s) or cable(s) within the at least one electrical conductor is/are provided with free ends such that it may be directly connected to the at least one electrode, in one embodiment by pressing such as pressing or swaging, such that a firmly-bonded connection is achieved. This embodiment is advantageous if one electrical conductor is assembled with multiple electrodes, such as multiple ring electrodes. That is to say, each electrical conductor includes multiple partial openings in the electrical insulation and to each partial opening an electrode is connected.

In one embodiment, the wire(s) or cable(s) within the one or more partial opening(s) of the electrical conductor(s) is/are mechanically or laser cut. In this embodiment, one or both of the free ends of the cut wire(s) or cable(s) can be connected to the one or more electrode(s).

It is appreciated that one or both of the free ends of the cut wire(s) or cable(s) is/are pressed or welded, in one embodiment before connecting one or both of the free ends of the cut wire(s) or cable(s) to the one or more electrode(s).

In one embodiment, the wire(s) or cable(s) within the one or more partial opening(s) of the electrical conductor(s) is/are mechanically or laser cut According to another aspect of one embodiment, a method for preparing an electrode-electrical conductor system for a medical device as defined herein is provided. The method includes the steps of a) providing at least one electrical conductor including one or more wire(s) or cable(s) which is/are surrounded by an electrical insulation, b) partially opening the electrical insulation of the at least one electrical conductor by laser ablation or mechanical cutting such as to obtain one or more partial opening(s) on one side of the wire(s) or cable(s), wherein the wire(s) or cable(s) are cut or uncut, and c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

As regards the at least one electrical conductor, the at least one electrode, and in one embodiments thereof, it is referred to the comments provided above when discussing the electrode-electrical conductor system in more detail.

According to step b), the electrical insulation of the at least one electrical conductor is partially opened by laser ablation or mechanical cutting such as to obtain one or more partial opening(s) on one side of the wire(s) or cable(s). In one embodiment, the electrical insulation of the at least one electrical conductor is partially opened by laser ablation such as to obtain one or more partial opening(s) on one side of the wire(s) or cable(s).

It is appreciated that the laser ablation or mechanical cutting of the electrical insulation of the at least one electrical conductor results in one or more partial opening(s) on one side of the wire(s) or cable(s). That is to say, the one or more partial opening(s) are such that they are only partially surrounding the wire(s) or cable(s). It is appreciated that the partial opening of the electrical insulation increases the dielectric strength/resistance against electrical short circuits towards other insulated conductors within the electrode-electrical conductor system.

Laser ablation relates to a process of removing material from a solid surface by irradiating the surface with a laser beam. The material of the irradiated surface evaporates, sublimates, and/or is converted to a plasma. The laser ablation step may be carried out using a galvanometer scanner and/or a x-, y-, z- and rotation-axis for the positioning the laser on the surface of the monolithic substrate or the electrode, respectively. Laser ablation and the equipment therefor are known to the skilled person.

According to one embodiment, the laser ablating in step b) is carried out with a nanosecond laser or pulsed laser, in one embodiment with an ultrashort pulsed laser.

According to one embodiment, the laser ablating is carried out with a laser pulse repetition rate of 50 to 500 kHz, and in one embodiment in the range of 100 to 200 kHz, and/or a laser pulse duration of 100 fs to 10 ns, and in one embodiment in the range of 500 to 1500000 fs, and/or a laser pulse energy in the range of 100 nJ to 100 µJ, and in one embodiment 500 nJ to 20 µJ.

According to one embodiment, the laser ablating is carried out with a laser pulse repetition rate of 50 to 500 kHz, and in one embodiment in the range of 100 to 200 kHz, and a laser pulse duration of 100 fs to 10 ns, and in one embodiment in the range of 500 to 1500000 fs, and a laser pulse energy in the range of 100 nJ to 100 µJ, and in one embodiment 500 nJ to 20 µJ.

It is appreciated that the one or more partial opening(s) suitable for mechanically and electrically connecting the at least one electrode to the at least one electrical conductor is/are added into the electrical insulation of the at least one electrical conductor where the at least one electrode is to be connected to the wire(s) or cable(s) of the at least one electrical conductor.

Furthermore, the number of partial opening(s) suitable for mechanically and electrically connecting the at least one electrode to the at least one electrical conductor added into the electrical insulation of the at least one electrical conductor depends on the number of electrode(s) connected thereto. In one embodiment, the number of partial opening(s) suitable for mechanically and electrically connecting the at least one electrode to the at least one electrical conductor added into the electrical insulation of the at least one electrical conductor corresponds to the number of electrode(s) connected thereto.

It is further appreciated that the partial openings can be aligned with each other in order to specifically arrange the electrode(s) on the electrical conductor.

As already mentioned above, the electrical conductor may include one or more bundle(s) or strand(s) of electrically insulated wire(s) or cable(s). In this embodiment, each of the one or more bundle(s) or strand(s) of electrically insulated wire(s) or cable(s) is in one embodiment surrounded by an outer electrical insulation covering each of the one or more bundle(s) or strand(s) of electrically insulated wire(s) or cable(s).

If such outer insulation is present, it is preferred that the outer electrical insulation of the at least one electrical conductor is circumferentially opened by laser ablation or mechanical cutting such as to obtain one or more opening(s) surrounding the at least one electrical conductor. In one embodiment, the outer electrical insulation of the at least one electrical conductor is circumferentially opened by laser ablation such as to obtain one or more opening(s) surrounding the at least one electrical conductor.

If such outer insulation is present, it is preferred that the outer insulation is ablated or cut circumferentially. This is advantageous as a pocket in the outer insulation is created, which receives the ring-electrode/electrode-segment after final diameter reduction by swaging, such that an isodiametric transition between electrode and outer coating is ensured.

According to step c) of the present method, the at least one electrode(s) is/are connected to the wire(s) or cable(s) via the one or more partial opening(s) of the at least one electrical conductor by welding, pressing, swaging, adhesives, brazing, soldering and/or dimples, whereby a mechanical and electrical connection between the at least one electrode to the at least one electrical conductor is achieved.

In one embodiment at least one electrode(s) is/are connected to the wire(s) or cable(s) via the one or more partial opening(s) of the at least one electrical conductor by welding, pressing, swaging, adhesives, brazing, soldering and/or dimples, whereby a mechanical and electrical connection between them is formed in a firmly-bonded and/or force-locked manner. In one embodiment, at least one electrode(s) is/are connected to the wire(s) or cable(s) via the one or more partial opening(s) of the at least one electrical conductor by welding, pressing, swaging, adhesives, brazing, soldering and/or dimples, whereby a mechanical and electrical connection between them is formed in a firmly-bonded manner.

In one embodiment, at least one electrode(s) is/are connected to the wire(s) or cable(s) via the one or more partial opening(s) of the at least one electrical conductor by welding, e.g. laser welding.

Such methods are well known to the skilled person.

In one embodiment of the present method, the at least one electrode(s) is/are connected to the uncut wire(s) or cable(s) via the one or more partial opening(s) of the at least one electrical conductor by welding, pressing, swaging, adhesives, brazing, soldering and/or dimples. Thus, the opening of the electrical insulation by laser ablation or mechanical cutting is in one embodiment carried out such that the wire(s) or cable(s) are uncut.

In this embodiment, it is appreciated that the wire(s) or cable(s) within the electrical conductor is/are uncut in step b).

Thus, in one embodiment, the method for preparing the electrode-electrical conductor system for a medical device includes the steps of
 a) providing at least one electrical conductor including one or more wire(s) or cable(s) which is/are surrounded by an electrical insulation,
 b) partially opening the electrical insulation of the at least one electrical conductor by laser ablation or mechanical cutting such as to obtain one or more partial opening(s) on one side of the wire(s) or cable(s), wherein the wire(s) or cable(s) are uncut, and c) connecting one or more electrode(s) to the uncut wire(s) or cable(s) of step b) via the one or more partial opening(s) in the electrical insulation of the at least one electrical conductor by welding, pressing, swaging, adhesives, brazing, soldering and/or dimples.

In another embodiment, the at least one electrode is connected to one or both free ends of the cut wire(s) or cable(s) of the at least one electrical conductor. In one embodiment, at least one electrode is connected to both free ends of the cut wire(s) or cable(s) of the at least one electrical conductor.

In this case, the method includes a further step of cutting the one or more wire(s) or cable(s) by laser cutting or mechanical cutting to obtain two free ends at the cut of the wire(s) or cable(s) before connecting the one or more electrode(s) to the one or more partial opening(s) of the at least one electrical conductor. It is appreciated that this step is in one embodiment carried out after step b).

In one embodiment, the partial opening of the electrical insulation of the at least one electrical conductor by laser ablation or mechanical cutting and the cutting of the one or more wire(s) or cable(s) by laser cutting or mechanical cutting can be carried out in the same step, i.e. by using the same machine/equipment.

Thus, in one embodiment, the method for preparing the electrode-electrical conductor system for a medical device includes the steps of
d) providing at least one electrical conductor including one or more wire(s) or cable(s) which is/are surrounded by an electrical insulation,
e) partially opening the electrical insulation of the at least one electrical conductor by laser ablation or mechanical cutting such as to obtain one or more partial opening(s) on one side of the wire(s) or cable(s), and cutting the one or more wire(s) or cable(s) by laser cutting or mechanical cutting to obtain two free ends at the cut of the wire(s) or cable(s), and
f) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

It is to be noted that the step of cutting the one or more wire(s) or cable(s) by laser cutting or mechanical cutting to obtain two free ends at the cut of the wire(s) or cable(s) is carried out such that the remaining electrical insulation surrounding the wire(s) or cable(s) is/are uncut. i.e. the electrical insulation located on the electrical conductor opposite the partial opening(s) in the electrical insulation of the at least one electrical conductor. Thus, it is appreciated that the at least one electrical conductor is only partially cut.

Additionally, the method may include a further step of lifting one or both of the free ends relative to the rest of the one or more wire(s) or cable(s) before attaching the one or more electrode(s) to the one or more partial opening(s) of the at least one electrical conductor. In one embodiment the method includes a further step of lifting both free ends relative to the rest of the one or more wire(s) or cable(s) before attaching the one or more electrode(s) to the one or more partial opening(s) of the at least one electrical conductor. It is appreciated that this step is only possible, if the one or more wire(s) or cable(s) of the electrical conductor is/are cut.

Thus, in one embodiment, the method for preparing the electrode-electrical conductor system for a medical device includes the steps of a) providing at least one electrical conductor including one or more wire(s) or cable(s) which is/are surrounded by an electrical insulation,
b) partially opening the electrical insulation of the at least one electrical conductor by laser ablation or mechanical cutting such as to obtain one or more partial opening(s) on one side of the wire(s) or cable(s), and cutting the one or more wire(s) or cable(s) by laser cutting or mechanical cutting to obtain two free ends at the cut of the wire(s) or cable(s), and lifting one or both of the free ends relative to the rest of the one or more wire(s) or cable(s), and
c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

If the method includes a step of cutting the one or more wire(s) or cable(s) by laser cutting or mechanical cutting to obtain two free ends at the cut of the wire(s) or cable(s), and optionally lifting one or both of the free ends relative to the rest of the one or more wire(s) or cable(s), the method may include a further step of pressing or welding one or both of the free ends, in one embodiment both of the free ends. For example, the method includes a further step of welding one or both of the free ends, in one embodiment, both of the free ends. Such a step is in one embodiment, carried out before connecting the one or more electrode(s) to the wire(s) or cable(s) via the one or more partial opening(s) of the at least one electrical conductor by welding, pressing, swaging, adhesives, brazing, soldering and/or dimples in step c).

Thus, in one embodiment, the method for preparing the electrode-electrical conductor system for a medical device includes the steps of a) providing at least one electrical conductor including one or more wire(s) or cable(s) which is/are surrounded by an electrical insulation,
b) partial opening the electrical insulation of the at least one electrical conductor by laser ablation or mechanical cutting such as to obtain one or more partial opening(s) on one side of the wire(s) or cable(s), and cutting the one or more wire(s) or cable(s) by laser cutting or mechanical cutting to obtain two free ends at the cut of the wire(s) or cable(s), and lifting one or both of the free ends relative to the rest of the one or more wire(s) or cable(s), and pressing or welding one or both of the free ends, and
c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

In one embodiment, the at least one electrical conductor of step a) may be partially or essentially completely covered with a polymer substrate such that the at least one electrical conductor is at least partially embedded in the polymer substrate.

It is preferred that the at least one electrical conductor is covered with the polymer substrate before step a) by well known methods. For example, the at least one electrical conductor is covered and molded or hot pressed (or laminated) with the polymer substrate.

In this case, step b) of the present method further includes opening the polymer substrate in which the electrical conductor is embedded by laser ablation or mechanical cutting.

In one embodiment, the opening of the polymer substrate can be carried out by laser cutting or mechanical cutting. For this, the biocompatible substrate is in one embodiment laser cut.

In one embodiment, the opening of the polymer substrate by laser cutting or mechanical cutting is carried out in the same step as the partial opening of the electrical insulation of the at least one electrical conductor by laser ablation or mechanical cutting and, if present, the cutting of the one or more wire(s) or cable(s), i.e. by using the same machine/equipment.

Thus, in one embodiment, the method for preparing the electrode-electrical conductor system for a medical device includes the steps of
- a) providing at least one electrical conductor including one or more wire(s) or cable(s) which is/are surrounded by an electrical insulation and a polymer substrate,
- b) opening the polymer substrate in which the electrical conductor is embedded by laser ablation or mechanical cutting and partially opening the electrical insulation of the at least one electrical conductor by laser ablation or mechanical cutting such as to obtain one or more partial opening(s) on one side of the wire(s) or cable(s), and cutting the one or more wire(s) or cable(s) by laser cutting or mechanical cutting to obtain two free ends at the cut of the wire(s) or cable(s), and lifting one or both of the free ends relative to the rest of the one or more wire(s) or cable(s), and pressing or welding one or both of the free ends, and
- c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

In one embodiment, the method for preparing the electrode-electrical conductor system for a medical device includes the steps of
- a) providing at least one electrical conductor including one or more wire(s) or cable(s) which is/are surrounded by an electrical insulation and a polymer substrate,
- b) opening the polymer substrate in which the electrical conductor is embedded by laser ablation or mechanical cutting and partially opening the electrical insulation of the at least one electrical conductor by laser ablation or mechanical cutting such as to obtain one or more opening(s) on one side of the wire(s) or cable(s), wherein the wire(s) or cable(s) are uncut, and
- c) connecting one or more electrode(s) to the wire(s) or cable(s) of step b) via the one or more partial opening(s) in the electrical insulation of the at least one electrical conductor by welding, pressing, swaging, adhesives, brazing, soldering and/or dimples.

In step c), the one or more electrode(s) is/are connected to the wire(s) or cable(s) of step b) via the one or more partial opening(s) in the electrical insulation of the at least one electrical conductor by welding, pressing, swaging, adhesives, brazing, soldering and/or dimples.

It is preferred to connect a ring electrode to the wire(s) or cable(s) of step b) via the one or more opening(s) in the electrical insulation of the at least one electrical conductor, in one embodiment, via a bridge including a metal or a conductive polymer, e.g. the polymer substrate.

If the bridge includes a metal, the bridge is in one embodiment attached to the wire(s) or cable(s) of the electrical conductor by a first weld, and to the ring electrode by a second weld. In one embodiment, such a bridge attached to the wire(s) or cable(s) of the electrical conductor by methods described in EP3185248A1 or EP3185363A1.

In step c) of the method, the ring electrode(s) is/are positioned around the electrical conductor obtained in step b) at the position of the one or more partial opening(s). For this, two or more opening(s) in the electrical insulation of the at least one electrical conductor may be aligned with each other. The positioning of the ring electrode(s) may be done by any suitable means known to the skilled person.

The ring electrode(s) may be attached to the wire(s) or cable(s) of the electrical conductor thereby selectively connecting the ring electrode(s) to the electrical conductor via the one or more partial opening(s) in the electrical insulation of the at least one electrical conductor.

According to one embodiment, the one or more electrode(s) is/are attached in step c) by swaging or welding, in one embodiment, by welding. According to another embodiment, the one or more electrode(s) is/are attached in step c) by swaging and welding.

The method according to one embodiment may include additional process steps of capping one end of the electrical conductor, adding fixing or spacer elements to system, surface structuring of the one or more electrode(s), and the like. Such processes are known to the skilled person and can be selected and adjusted according to the desired application of the electrode-electrical conductor system, in one embodiment, to the desired application in a medical device.

The features disclosed in the claims, the specification, and the drawings maybe essential for different embodiments, both separately and in any combination with each other.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. An electrode-electrical conductor system for a medical device comprising:
- a) at least one electrical conductor comprising one or more wire(s) or cable(s) covered by electrical insulation, wherein the electrical insulation comprises one or more partial opening(s), which is/are arranged on one side of the wire(s) or cable(s), and
- b) one or more electrode(s), which is/are mechanically and electrically connected to the wire(s) or cable(s) via the one or more partial opening(s) arranged on one side of the wire(s) or cable(s) by at least one of welding, pressing, swaging, adhesives, brazing, soldering and dimples.

2. The electrode-electrical conductor system according to claim 1, wherein the electrical conductor comprises one or more bundle(s) or strand(s) of electrically insulated wire(s) or cable(s), each of the one or more bundle(s) or strand(s) of electrically insulated wire(s) or cable(s) is/are covered by an electrical insulation, which comprises one or more opening(s) arranged on the one or more partial opening(s) on one side of the wire(s) or cable(s).

3. The electrode-electrical conductor system according to claim 1, wherein the wire(s) or cable(s) of the electrical conductor and/or the at least one electrode comprise(s) one or more of the metals Pt, Ir, Ta, Pd, Ti, Fe, Au, Mo, Nb, W, Ni, Ti, Ag, Cu, or a mixture or alloy thereof or the electrical conductor or the at least one electrode is/are a multilayered material system(s).

4. The electrode-electrical conductor system according to claim 1, wherein the electrical insulation of the electrical conductor comprises an insulating plastic material selected from the group comprising polyethylene, polyurethane, polyimide, polyamide, PEEK, and fluorinated plastic materials such as ETFE, PTFE, PFA, PVDF, FEP or FPO, and mixtures thereof.

5. The electrode-electrical conductor system according to claim 1, wherein the wire(s) or cable(s) has/have a thickness in the range from 5 to 250 μm, and the electrical insulation of the wire(s) or cable(s) has/have a thickness in the range from 3 to 150 μm.

6. The electrode-electrical conductor system according to claim 1, wherein the wire(s) or cable(s) has/have a thickness in the range from 10 to 120 μm, and the electrical insulation of the wire(s) or cable(s) has/have a thickness in the range from 5 to 70 μm.

7. The electrode-electrical conductor system according to claim 1, wherein the wire(s) or cable(s) within the one or more partial opening(s) is/are mechanically or laser cut such that one or both of the free ends of the cut wire(s) or cable(s) is/are connected to the one or more electrode(s).

8. The electrode-electrical conductor system according to claim 7, wherein one or both of the free ends of the cut wire(s) or cable(s) is/are pressed or welded.

9. The electrode-electrical conductor system according to claim 1, wherein the one or more electrode(s) is/are selected from a cubic, rectangular, cylindrical and ring electrode and ring electrode segment.

10. The electrode-electrical conductor system according to claim 1, wherein the electrical conductor is embedded in a biocompatible polymer substrate selected from the group comprising polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), kapton and mixtures thereof, comprising one or more opening(s) arranged on the one or more partial opening(s) on one side of the wire(s) or cable(s).

11. A method for preparing an electrode-electrical conductor system for a medical device according to claim 1, the method comprising:
a) providing the at least one electrical conductor comprising the one or more wire(s) or cable(s) which is/are surrounded by the electrical insulation,
b) partially opening the electrical insulation of the at least one electrical conductor by laser ablation or mechanical cutting such as to obtain the one or more partial opening(s) on one side of the wire(s) or cable(s), wherein the wire(s) or cable(s) are cut or uncut, and
c) connecting the one or more electrode(s) to the wire(s) or cable(s) of step b) via the one or more partial opening(s) in the electrical insulation of the at least one electrical conductor by welding, pressing, swaging, adhesives, brazing, soldering and/or dimples.

12. The method according to claim 11, wherein the method further comprises cutting the one or more wire(s) or cable(s) by laser cutting or mechanical cutting to obtain two free ends at the cut of the wire(s) or cable(s) before attaching the one or more electrode(s) to the one or more partial opening(s) of the at least one electrical conductor.

13. The method according to claim 12, wherein the method further comprises lifting one or both of the free ends relative to the rest of the one or more wire(s) or cable(s) before attaching the one or more electrode(s) to the one or more partial opening(s) of the at least one electrical conductor.

14. The method according to claim 11, wherein the partial opening of the electrical insulation by laser ablation or mechanical cutting is carried out such that the wire(s) or cable(s) are uncut, and/or the further step of cutting the one or more wire(s) or cable(s) by laser cutting or mechanical cutting is carried out such that the remaining electrical insulation surrounding the wire(s) or cable(s) is uncut.

15. The method according to claim 12, wherein the method further comprises pressing or welding one or both of the free ends, preferably both of the free ends.

16. The method according to claim 11, wherein step b) further comprises opening a polymer substrate in which the electrical conductor is embedded by laser ablation or mechanical cutting.

* * * * *